(12) United States Patent
Bracken et al.

(10) Patent No.: US 7,504,093 B2
(45) Date of Patent: *Mar. 17, 2009

(54) COMPOSITION FOR TREATING HAIR

(75) Inventors: Gillian Bracken, Wirral (GB); Julie Hutchison Cooper, Bebington (GB); Paul John Cunningham, Wirral (GB); Paul Howard Neill, Chicago, IL (US); Robert George Riley, Wirral (GB); Sigrun Tollerton, Wrexham (GB)

(73) Assignee: Unilever Home & Personal Care USA division of Conopco, Inc., Chicago, IL (US)

( * ) Notice: Subject to any disclaimer, the term of this patent is extended or adjusted under 35 U.S.C. 154(b) by 560 days.

This patent is subject to a terminal disclaimer.

(21) Appl. No.: 10/346,474

(22) Filed: Jan. 17, 2003

(65) Prior Publication Data

US 2003/0161796 A1   Aug. 28, 2003

(30) Foreign Application Priority Data

Jan. 21, 2002  (EP)  .................................. 02250399
Aug. 28, 2002  (GB)  ................................. 0221034.2

(51) Int. Cl.
  *A61Q 5/00* (2006.01)
  *A61Q 5/06* (2006.01)
  *A61Q 5/10* (2006.01)
  *A61Q 5/12* (2006.01)

(52) U.S. Cl. .................. 424/70.12; 424/70.1; 424/70.2; 424/70.11; 424/70.15; 424/489

(58) Field of Classification Search .................. None
See application file for complete search history.

(56) References Cited

U.S. PATENT DOCUMENTS

| | | | |
|---|---|---|---|
| 4,861,583 A | 8/1989 | Sramek | |
| 5,051,489 A | 9/1991 | O'Lenick, Jr. | |
| 5,194,260 A * | 3/1993 | Grollier et al. | 424/401 |
| 5,656,280 A | 8/1997 | Herb et al. | |
| 5,665,687 A | 9/1997 | Khayat et al. | |
| 5,733,531 A | 3/1998 | Mitchnick et al. | |
| 6,048,520 A * | 4/2000 | Hoshowski | 424/70.17 |
| 6,132,736 A * | 10/2000 | Mellul et al. | 424/401 |
| 6,156,826 A | 12/2000 | Guénin et al. | |
| 6,211,125 B1 * | 4/2001 | Crudele et al. | 510/122 |
| 6,274,131 B1 * | 8/2001 | Piot et al. | 424/70.7 |
| 6,315,986 B1 | 11/2001 | Wong et al. | |
| 6,491,902 B2 * | 12/2002 | Shefer et al. | 424/70.1 |
| 6,516,826 B2 * | 2/2003 | Allen | 137/118.04 |
| 6,582,679 B2 * | 6/2003 | Stein et al. | 424/47 |
| 2003/0059377 A1* | 3/2003 | Riley | 424/47 |

FOREIGN PATENT DOCUMENTS

| | | |
|---|---|---|
| EP | 0 346 852 B1 | 12/1989 |
| EP | 0 412 865 A1 | 2/1991 |
| EP | 0 506 197 B2 | 7/2001 |
| WO | 01/39729 A1 | 6/2001 |
| WO | 01/73412 A1 | 10/2001 |

OTHER PUBLICATIONS

European Search Report (EP 02 25 0399).
Patent Abstract of Japan (JP 11228359).
Co-pending application Bracken et al.; U.S. Appl. No. 10/346,472, filed Jan. 17, 2003; entitled "Hair Treatment Composition".

* cited by examiner

*Primary Examiner*—Jyothsna A Venkat
(74) *Attorney, Agent, or Firm*—Karen E. Klumas

(57) ABSTRACT

A hair treatment composition comprises particles having a first non-aqueous phase and, retained within said first non-aqueous phase, a second hydrophilic phase which is an aqueous solution, dispersion, emulsion or a solid or liquid having a log P value less than 1, said second phase comprising a hair benefit agent, wherein said first non-aqueous phase has a melting point of from 30° C. to 100° C.

13 Claims, No Drawings

COMPOSITION FOR TREATING HAIR

This invention relates to a hair treatment composition, to a method of treating hair and to the use of certain materials for conditioning hair.

Rinse off hair treatment compositions are products which are intended to be rinsed from the hair during use, normally with water, after they have been applied to the hair by the user. Typically, it is desirable to deposit any beneficial agents onto the hair and not to remove all of these agents during the rinsing step. This deposition can be achieved, for example, by using cationic polymers. Rinse off treatment compositions include shampoos and hair conditioners.

Leave on hair treatment products, such as products for styling hair, are not intended to be rinsed from the hair immediately after use. The products may contain hair benefit agents that deposit onto the hair together with the agent that is responsible for the styling properties of the product.

When a hair benefit agent is applied to the hair from a rinse off or leave on product, it can be useful to cause the hair benefit agent to become active, that is to say to exhibit its beneficial effect to a greater extent, not immediately on application but only after a trigger for the activation of the agent. For example, it can be desirable to activate a hair benefit agent only after the hair is heated. This allows the hair benefit agent to be delivered to the hair at a later stage from the rest of the rinse off product. Also, the hair benefit agent can be protected from air and/or moisture until it is released.

A heat activated hair curling treatment composition is described in U.S. Pat. No. 4,861,583. The composition employs a certain linear or branched or cross-linked water soluble polyethylene oxide polymer having a melting point of 50 to 80° C. The polymer is exposed to heat from a curling iron and thereby imparts a curl to hair. There is no disclosure in this document of the delivery of any other benefit to the hair or of the use of other materials.

U.S. Pat. No. 6,156,826 relates to the encapsulation of perfumes in hydrophobic particles for controlled release. The perfumes that are encapsulated in the particles have a log P value of 1 to 8 and are, therefore, substantially insoluble in an aqueous phase. In the examples which are given in the document, vegetable waxes are used to encapsulate the perfume and there is no mention of any benefit being associated with the waxes themselves.

WO 01/73412 discloses the optional use of visible particles in hair conditioning compositions. The particles are not intended to be melted when the hair is heated and are of a substance that can be broken and disintegrated with very little shear with the fingers on use and is typically a polysaccharide, oligosaccharide or monosaccharide.

U.S. Pat. No. 5,656,280 discloses water-in-oil-in-water emulsion compositions which can be used to deliver agents to the hair and/or the skin.

There remains a need for systems that can deliver hair benefit agents to the hair after a heat treatment step, providing benefits other than the delivery of hydrophobic materials such as perfumes.

It is known that certain types of solid particles can be employed in hair treatment compositions. For example, U.S. Pat. No. 5,051,489 discloses silanol waxes that can be used in a range of different applications, including to lubricate hair. WO 01/39729 discloses wax particles having a size of from 10 to 300 nm as reviving agents for hair treatment products. EP-A-0346852 describes oil-in-water emulsions containing 1% to 6% by weight of an oil or wax. EP-A-506197 teaches solid lipid particles having a size of 50 nm to 1000 nm for the treatment of hair. There is no mention in any of these documents of heat treatment of the hair, after the particles have been deposited onto the hair.

JP-A-11-228,359 describes a shampoo composition containing wax particles having a size of 1 micron (1 μm) or less and a melting point of 50 to 100° C. The particles are said to provide softness, combing and antistatic benefits to hair. Again, there is no indication in the document that heating the particles is necessary in order to achieve the benefits.

The present invention is based on the discovery of a system for providing heat activated benefits in hair compositions that has surprising advantages over the compositions of the prior art. In particular, the invention is based on compositions that deliver surprisingly effective hair conditioning benefits, and optionally other benefits, when applied to the hair.

According to the present invention, there is provided a hair treatment composition comprising particles having a first non-aqueous phase and, retained within said first non-aqueous phase, a second hydrophilic phase which is: an aqueous solution, dispersion or emulsion; or a solid or liquid having a log P value (wherein P is the n-octanol/water partition coefficient) less than 1, said second phase comprising a hair benefit agent, wherein said first non-aqueous phase has a melting point of from 30° C. to 100° C.

In another aspect, the invention provides a method of treating hair which comprises applying to the hair a composition of the invention and heating the hair to a temperature above the melting point of the first non-aqueous phase.

Yet another aspect of the invention is a method of conditioning hair which comprises applying to the hair particles comprising a non-aqueous phase having a melting point of from 30° C. to 100° C. and heating hair treated with the particles to a temperature above the melting point of the non-aqueous phase.

The invention also relates to a method of manufacturing a hair treatment composition of any preceding claim comprising the following steps:
  i) heating the non aqueous phase so it becomes molten;
  ii) adding the second hydrophilic phase to the non aqueous phase;
  iii) heating the remainder of the composition to a temperature on or below the solidification commencement temperature of the non aqueous phase; and
  iv) then adding the resulting mixture of step ii) to the heated composition of iii).

This method of manufacture maximises the capture of the material to be encapsulated.

An alternative to the above method of manufacture is to replace step iii) by heating the remainder of the composition to a temperature on or above the melting point of the non aqueous phase (the wax). Preferably the temperature of the wax is raised to a maximum of 20° C. its melting point, more preferably the temperature of the wax is raised to a maximum of 10° C. above its melting point. This method of manufacture means that particles having the required particle size are formed.

It is preferable if the sequence of addition in these processes is as listed above Although not preferred in some instances other components may be included in these formulations.

The solidification temperature is the temperature at which the viscosity of the molten non aqueous phase begins to significantly increase upon cooling at ambient temperature and at 1 atmosphere pressure.

The melting point of the non aqueous phase (in most cases this means the wax) is measured by DSC(Differential Scanning Calorimetry). The melting point referred to in this specification is the peak of the curve obtained by DSC.

A further aspect of the invention is the use of particles comprising a non-aqueous phase having a melting point of from 30° C. to 100° C. for conditioning hair by heating hair treated with particles to a temperature above the melting point of the non-aqueous phase. Conditioning benefits include ease of comb, smoothness, softness, body, volume, bounce, fullness and texture.

The invention is based on the discovery that it is possible to deliver a hair benefit agent from particles, when the agent is relatively hydrophilic and, surprisingly, that the particles can deposit effectively from hair treatment products. The particles can provide one property or a combination of two or more properties that are beneficial to the hair after heat treatment of the hair, for example during heat styling or drying at an elevated temperature. Particularly preferred are particles that can provide hair conditioning and hair styling benefits and which can be delivered from a shampoo or rinse conditioner composition. The invention is also based on the finding that particles are capable of being effectively deposited onto hair and, following heat treatment of the hair to melt the particles, can provide conditioning benefits to hair. In certain embodiments, the invention involves the unexpected finding that melting the particles is capable of delivering hydrophilic materials to the hair, in spite of the hydrophobic exterior of the particles.

The melting of the non-aqueous phase of the particles provides at least part of the conditioning benefits of the composition (such as ease of comb), whilst any hair benefit agent that is retained in the particles can provide a benefit, which may be a conditioning benefit or another hair care benefit, after it has been released from the particles on melting the non-aqueous phase.

The non-aqueous phase of the particles of the invention typically comprises less than 1% by weight based on the weight of the non-aqueous phase of water, more preferably less than 0.1% by weight water. The non-aqueous phase is typically of a material that is deformable at room temperature and preferably does not become broken and disintegrated with normal shear with the fingers on use. Thus, when hair benefit agents are present in the non-aqueous phase, they are preferably substantially not released (ie, more than 50%, preferably more than 75%, more preferably more than 95% by weight of the materials remain retained) until the hair is heated.

The non-aqueous phase is typically a hydrophobic material, such as a wax. Suitable waxes include: silicones; triglycerides such as synthetic or natural substances; lipid materials such as carboxylic acids, alcohols and esters containing from 12 to 48 carbon atoms eg, stearyl stearate; hydrocarbon waxes; and hydrophobic polymers and copolymers. Mixtures of these substances may also be used.

The chemical identity of the wax is less important than the physical properties of the wax and suitable waxes include those from synthetic and natural sources. The waxes may be polymeric or non-polymeric. Preferably, the wax is selected from naturally occurring waxes, synthetic hydrocarbon waxes, synthetic silicone waxes and mixtures thereof. Naturally occurring waxes may be obtained directly or indirectly from natural plant (ie, vegetable), animal or mineral sources. Suitable waxes from natural sources include those based on triglycerides, for example waxes obtained by the hydrogenation of vegetable oil, animal fats and oils and natural waxes from plants. Suitable synthetic waxes include silicone waxes and hydrocarbon waxes. Modified fatty acid (fatty acids include carboxylic acids containing from 12 to 24 carbon atoms) glycerol esters are also suitable for use in the invention. Waxes may contain substantially one chemical compound or a mixture of chemical compounds and can be used singly or as a mixture of two or more different waxes. Particularly preferred are vegetable waxes Examples of other waxes that are suitable for use in the invention include beeswax, cotton wax, bayberry wax, Chinese wax, spermaceti, montan wax, rice bran wax, lanolin, kapok wax, lanolin acetate or other lanolin esters and/or ethers, sugar cane wax, hexyl laurate, jojoba wax, shellac, paraffin wax, cholesterol, hydrogenated castor oil, petrolatum, cacao butter, coconut oil, palm oil, palm kernel oil, and the like, optionally hydrogenated where this is not already specified and where this is appropriate in order to increase the melting point of the wax.

The waxes may contain liquid fats and/or oils, provided that the wax remains substantially solid (which term includes self-supporting soft solids) at room temperature (25° C.). Liquid fats and oils include triglyceride oils from plant sources, such as for example avocado oil, olive oil, corn oil, rape seed oil, sesame oil, wheat germ oil, castor oil, linseed oil, sunflower oil, cottonseed oil, soybean oil, peanut oil, tea tree oil, jojoba oil and the like. Other liquid oils include fatty acids (ie, acids having more than 10 and typically less than 30 carbon atoms), fatty alcohols (ie, alcohols having more than 10 carbon atoms and typically less than 30) and fatty acid esters (ie, esters formed between C1-C10 alcohols or fatty alcohols and fatty acids, generally containing up to 48 carbon atoms), for example butyl myristate, cetyl palmitate, decyl oleate, glyceryl laurate, glyceryl ricinoleate, glyceryl stearate, glyceryl isostearate, hexyl laurate, isobutyl palmitate, isocetyl stearate, isopropyl isostearate, isopropyl laurate, isopropyl linoleate, isopropyl myristate, isopropyl palmitate, isopropyl stearate, propylene glycol monolaurate, propylene glycol ricinoleate, propylene glycol stearate, propylene glycol isostearate, behenic acid, palmitic acid, stearic acid, behenyl alcohol, cetyl alcohol, isocetyl alcohol and mixtures thereof.

A suitable material for the non-aqueous phase is silicone wax.

The silicone wax that is preferably used in the invention comprises one or more $C_3$ to $C_{40}$, branched or unbranched, saturated or unsaturated, optionally substituted hydrocarbon groups. Preferably, the hydrocarbon groups contain 6 to 40 carbon atoms, more preferably 10 to 36 carbon atoms. The hydrocarbon groups may be fully saturated ie, alkyl groups. Alternatively, the hydrocarbon groups may be unsaturated and may comprise one, two or more carbon-carbon double or triple bonds ie, they may be alkenyl or alkynyl groups. The hydrocarbon groups are optionally substituted, for example with one or more substituents selected from hydroxyl, amino, carboxyl and phenyl. Examples of unbranched (ie, linear) alkyl groups are propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosanyl, heneicosanyl, docosanyl, tricosanyl and tetracosanyl. The silicone wax may contain a single alkyl group or a mixture of different alkyl groups.

The silicone wax will also preferably contain the repeat unit ($-O-Si(CH_3)_2-$).

Silicone waxes include those with $C_3$ to $C_{40}$ alkyl or alkoxy groups bonded to the end of the silicone polymer chain, as well as those with $C_3$ to $C_{40}$ alkyl or alkoxy groups grafted or otherwise attached along the silicone polymer chain. Silicone waxes may comprise alkyl or alkoxy groups both at the end of the polymer chain and along the backbone of the polymer chain.

Therefore, the silicone wax may have the general formula:

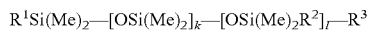

wherein $R^1$, $R^2$ and $R^3$ are independently $C_3$ to $C_{40}$ branched or unbranched alkyl or alkoxy groups, k and l are independently integers from 0 to 100, provided that k+l is at least 4, and, when k and l are both not equal to zero, the polymer can comprise random or block arrangements of l and k groups.

Suitable examples of other silicone waxes that may be used in the invention include silicone copolymers having the average structural formulae:

  1.

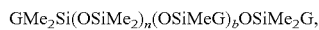  2.

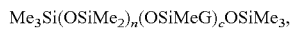  3.

or

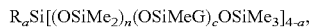  4.

in which formulae $R_a$ is a hydrocarbon group free of aliphatic unsaturation and has from 1 to 10 carbon atoms.
Me is a methyl group, in these formulae and throughout this specification,
G is a radical of the structure —D(OR")$_m$A wherein D is an alkylene group containing from 1 to 40 carbon atoms,
R" is composed of ethylene groups and groups selected from propylene and butylene groups, preferably the amount of ethylene radicals relative to other alkylene groups being such that the ratio of carbon atoms to oxygen atoms in the total OR" blocks ranges from 2.3:1 to 2.8:1,
m has an average value from 0 to 100, preferably 7 to 100,
A is a radical selected from —OR', —OOCR' and —OC(O)OR' radicals wherein R' is a radical free of aliphatic unsaturation selected from hydrocarbon and hydrocarbonoxy radicals, the A radical containing a total of less than eleven atoms.
a has an average value from 0 to 1,
n has an average value from 0 to 500, preferably 6 to 420,
d has an average value of from 0 to 30,
b has an average value from 0 to 50, preferably 1 to 30, and
c has an average value from 0 to 50, preferably 3 to 30, provided that at least one of $R_a$, R", D, A and R' contains at least 3 carbon atoms. Preferably, the copolymers contain at least 13 percent by weight $OSiMe_2$ units based on the weight of the copolymer.

These polymers and methods for their production are disclosed in EP-A-0583130 and U.S. Pat. No. 3,402,192, the contents of which are incorporated by reference herein.

Other examples of silicone waxes that are suitable for use in the invention are the compounds of the formula:

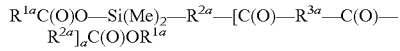

wherein $R^{2a}$ is —[OSi(Me) ($R^{4a}$)]$_b$—OSi (Me)$_2$O—,
$R^{1a}$ is alkyl having from 6 to 40 carbon atoms,
$R^{3a}$ is —(CH$_2$)$_c$— or —(CH$_2$)$_d$—CH=CH—(CH$_2$)$_e$,
a is an integer from 0 to 20,
b is an integer of from 1 to 200,
c, d and e are independently integers from 1 to 10, and
$R^{4a}$ is alkyl having from 1 to 18 carbon atoms or phenyl.

The silicone polymers mentioned above and methods for their production are described in U.S. Pat. No. 5,051,489, the contents of which are incorporated by reference herein.

Preferred examples of silicone waxes are: stearyl, cetyl and behenyl dimethicone or trimethicone; stearoxy or behenoxy dimethicone or trimethicone; mono-, di- or tri-$C_3$ to $C_{40}$ alkyl polysiloxanes; and mono-, di- or tri-$C_3$-$C_{40}$ alkoxy polysiloxanes; mono-, di- or tri-$C_4$-$C_{41}$ acyl polysiloxanes. In particular those which contain a [OSi(Me)$_2$] repeat unit in which the average number of the repeat units is from 4 to 10, such as 5 to 9, for example 7. Suitable silicone waxes are, for example, available from Goldschmidt GmbH under the trade mark Abil eg, Abil 2440 and Abil 9810.

The silicone wax used in the particles of the invention can be a single compound or a mixture of two or more different compounds.

The non-aqueous phase has a melting point of from 30° C. to 100° C. Preferably, the melting point is from 35° C. to 90° C., more preferably 40° C. to 70° C. such as 45° C. to 60° C. The melting point of the non-aqueous phase is the temperature at which the majority (ie, greater than 50% by weight, more preferably greater than 75% by weight) of the non-aqueous phase becomes liquid and is therefore able to flow. Above its melting point, the non-aqueous phase can spread onto hair fibres and thus can impart conditioning benefits to the hair. The melting point of the non-aqueous phase, as defined herein, is the melting point when it is in the particles of the invention ie, taking into account any other components in the particles which may raise or lower the observed melting point of the wax in the particles. Melting points can be determined by DSC (Differential Scanning Calorimetry), by observing the melting transition.

The non-aqueous phase may also comprise one or more other materials. The one or more other materials may be in the same phase as the non-aqueous phase or in a different phase, separate from the aqueous phase. Examples of one or more other materials that may be present in the non-aqueous phase, in addition to or separate from the materials mentioned hereinbefore, include: hydrocarbon oils and waxes, such as paraffin wax; hydrophobic polymers and copolymers melting in the temperature range of from 30° C. to 100° C.; silicone oils eg, linear polydimethylsiloxane; mineral oil; fragrance; amines, eg, stearyl amidopropyl dimethylamine; quaternary ammonium compounds as described hereinafter, for example comprising from 6 to 34 carbon atoms, such as those comprising a trimethyl ammonium group and a linear alkyl chain containing from 6 to 30 carbon atoms eg, cetyl trimethylammonium salts (such as the chloride salt), behenyl trimethylammonium salts (such as chloride), distearyldimethylammonium salts (such as chloride) and PEG-2 oleammonium salts (such as chloride); emulsifiers eg, nonionic, anionic or cationic surface active materials); solid particles such as clays, silicas, and polymers including natural and synthetic rubbers, thermoplastic polymers and PTFE; and mixtures therof.

The particles may be used in the present invention either alone or in combination with other particles containing the same or different non-aqueous phase and/or the same or different hydrophilic phase.

The weight ratio of non-aqueous phase to hydrophilic phase in particles of the invention is preferably from 10:1 to 1:10, more preferably from 5:1 to 1:5, such as from 2:1 to 1:2.

The hydrophilic phase is:
an aqueous solution, dispersion or emulsion; or
a solid or liquid having a log P value (wherein P is the n-octanol/water partition coefficient) less than 1. The hydrophilic phase comprises a hair benefit agent.

When the hydrophilic phase comprises an aqueous solution, dispersion or emulsion, water is preferably present in an amount of from 5% to 99% by weight of the hydrophilic phase, more preferably from 25% to 98% by weight, such as from 40% to 98% by weight. The term dispersion covers any mixture of water with one or more other hair benefit agents that contains more than one phase but is not an emulsion (including, for example, a suspension).

The solids or liquids that may be present in the hydrophilic phase have a log P value (wherein P is the n-octanol/water partition coefficient and log P means $\log_{10}$ P) of less than 1, preferably less than 0.5, more preferably less than 0. Log P values can be determined as described in J Sangster, Octanol-water partition coefficients of simple organic compounds, *J Phys Chem Ref Data*, 18, 1111, 1989, the contents of which are incorporated by reference herein, and are typically determined at 25° C. Preferably, log P values are measured at 25° C.

The hydrophilic phase is more hydrophilic than the non-aqueous phase.

Materials for incorporation in the hydrophilic phase may be single compounds or materials or mixtures of different compounds or materials. At least one compound or material is a hair benefit agent ie, is capable of imparting beneficial properties when used in a hair treatment product, including properties beneficial or desirable on the hair, benefits for the scalp and aesthetic, cosmetic or other benefits perceived by the user of the product. Benefits include, for example, hair conditioning, hair colouring, hair styling and antidandruff benefits. In one embodiment of the invention, hair conditioning and hair styling benefits are particularly preferred.

The hair benefit agent of the hydrophilic phase is preferably water-soluble or water-dispersible and includes both cosmetic and medicinal compounds that act upon contact with the skin or hair.

The one or more hair benefit agents of the hydrophilic phase are present in a sufficient amount to perform the intended function, typically in an amount of about 0.1% to about 30% by weight of the particles.

The hydrophilic phase therefore can comprise one or more of a cosmetic compound, a medicinally-active compound or any other compound that is useful upon topical application to the skin or hair. Such topically-active compounds include, but are not limited to, hair and skin conditioners, hair and skin cleansers, hair fixatives (including hair styling polymers), hair dyes, hair growth promoters, deodorants, skin care compounds, permanent wave compounds, hair relaxers, hair straighteners, antibacterial compounds, antifungal compounds, anti-inflammatory compounds, topical anesthetics, sunscreens and other cosmetic and medicinal topically-effective compounds.

A preferred material that is contained in the hydrophilic phase is a hair conditioner (which may be water soluble or dispersible at ambient temperature), such as a quaternary ammonium compound. Quaternary ammonium compounds are substantive to the hair and are excellent hair conditioners, but have a well-known incompatibility with anionic surfactants and anionic dyes. Therefore, quaternary ammonium compounds generally are not a component in shampoo-conditioner compositions or anionic dye-based compositions, but are applied to the hair from a separate conditioning composition.

The quaternary ammonium compounds have the general structural formula:

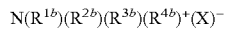

$N(R^{1b})(R^{2b})(R^{3b})(R^{4b})^+(X)^-$ wherein $R^{1b}$ is an alkyl group including from about 8 to about 18 carbon atoms; $R^{2b}$ is selected from the group consisting of an alkyl group including from about 8 to about 18 carbon atoms, a hydrogen atom, a methyl group, an ethyl group, a hydroxymethyl group and a hydroxyethyl group; $R^{3b}$ is selected from the group consisting of a benzyl group, a hydrogen atom, a methyl group, an ethyl group, a hydroxymethyl group and a hydroxyethyl group; $R^{4b}$ is selected from the group consisting of a hydrogen atom, a methyl group, an ethyl group, a hydroxymethyl group and a hydroxyethyl group; and X is an anion. The quaternary nitrogen of the water-soluble quaternary ammonium compound also can be a component of a heterocyclic nitrogen-containing moiety, such as morpholine or pyridine. The anion of the quaternary ammonium compound can be any common anion, such as chloride, methosulfate, ethosulfate, nitrate, bromide, tosylate, acetate, or phosphate.

The quaternary ammonium compounds have one or two long chain alkyl groups containing from about 8 to about 18 carbon atoms. The long chain alkyl groups also can include, in addition to, or in replacement of, carbon and hydrogen atoms, ether linkages or similar water-solubilizing linkages. The remaining two or three substituents of the quaternary nitrogen of the quaternary ammonium compound can be hydrogen; or benzyl; or short chain alkyl or hydroxyalkyl groups, such as methyl, ethyl, hydroxymethyl or hydroxyethyl groups; or combinations thereof, either of the same or different identity.

Exemplary quaternary ammonium compounds include, but are not limited to laurtrimonium chloride; Quaternium-16; lauralkonium chloride; olealkonium chloride; dilauryldimonium chloride; cetalkonium chloride; dicetyldimonium chloride; laurylpyridinium chloride; cetylpyridinium chloride; soyatrimonium chloride; Polyquaternium-6; Polyquaternium-7; guarhydroxypropyltrimonium chloride; Polyquaternium-11; Polyquaternium-5; Polyquaternium-10; Polyquaternium-24; cetrimonium chloride; Quaternium-24; mytrimonium chloride; PEG-2 cocomonium chloride; PEG-2 cocoyl quaternium-4; PEG-15 cocoyl quaternium-4; PEG-2 stearyl quaternium-4; PEG-15 stearyl quaternium-4; PEG-2 oleyl quaternium-4; and PEG-15 oleyl quaternium-4, and mixtures thereof, wherein the compound designation is provided by the Cosmetic, Toiletry and Fragrance Association, Inc. in the CTFA Cosmetic Ingredient Dictionary, 4th Ed., 1991, hereinafter referred to as the CTFA Dictionary. Other water-soluble quaternary ammonium compounds are listed in the CTFA Cosmetic Ingredient Handbook, 1st Ed., 1988 (hereinafter the CTFA Handbook) at pages 40-42, incorporated herein by reference.

Other hair conditioners also can be used in the hydrophilic phase. Such hair conditioners include, but are not limited to, fatty amine salts, ethoxylated fatty amine salts, dimethicone copolyols, protonated polyethylenimines, protonated ethoxylated polyethylenimines, soluble animal collagen, lauramine oxide, cationic polymers, numerous other water-soluble hair conditioners listed in the CTFA Handbook at pages 71-73, incorporated herein by reference, and mixtures thereof.

In addition to hair conditioners, a skin conditioner can be used as the hair benefit agent. Skin conditioning agents include, but are not limited to, humectants, such as fructose, glucose, glycerin, propylene glycol, glycereth-26, mannitol and urea; pyrrolidone carboxylic acid; hydrolyzed lecithin; coco-betaine; cysteine hydrochloride; glutamine; PPG-15; sodium gluconate; potassium aspartate; oleyl betaine; thiamine hydrochloride; sodium laureth sulfate; sodium hyaluronate; hydrolyzed proteins; hydrolyzed keratin; amino acids; amine oxides; water-soluble derivatives of vitamins A, E and D; amino-functional silicones; ethoxylated glycerin; alpha-hydroxy acids and salts thereof; water-soluble fatty oil derivatives, such as PEG-24 hydrogenated lanolin, almond oil, grape seed oil and castor oil; numerous other water-soluble skin conditioners listed in the CTFA Handbook, pages 79-84, incorporated herein by reference; and mixtures thereof.

The hair benefit agent also can be a hair fixative or film former that imparts style-retention properties to hair, i.e., sets the hair. Hair fixatives and film formers include the hair styling polymers described hereinafter as components of styling products. The hair fixative typically is a homopolymer, a copolymer, or a terpolymer. The polymers can be nonionic, amphoteric, anionic or cationic. Examples of hair fixatives include, but are not limited to, an acrylamide copolymer; an acrylamide/sodium acrylate copolymer; a polystyrene sulfonate; a polyethylene oxide; polyethylene oxide-polypropylene oxide random or block copolymer (eg, the Pluronic polymers, such as F108 and F127 available from BASF AG); a water-dispersible polyester; a cationic cellulose; an acrylate/ammonium methacrylate copolymer; an aminoethylacrylate phosphate/acrylate copolymer; a polyacrylamide; Polyquaternium-1; Polyquaternium-2; Polyquaternium-4; Polyquaternium-5; Polyquaternium-6; Polyquaternium-7; Polyquaternium-8; Polyquaternium-9; Polyquaternium-10; Polyquaternium-11; Polyquaternium-12; Polyquaternium-13; Polyquaternium-14; Polyquaternium-15; Polyquaternium-16; Polyquaternium-28; a PVP (polyvinylpyrrolidone) or a copolymer thereof; a PVP/dimethylaminoethylmethacrylate copolymer; a PVP/ethyl methacrylate/methacrylic acid copolymer; a carboxylated polyvinyl acetate; vinyl/caprolactam/PVP/dimethylaminoethyl methacrylate copolymer (GAFFIX VC713); a PVP/vinyl acetate copolymer; a sodium acrylate/vinyl alcohol copolymer; sodium carrageenan; a vinyl acetate/crotonic acid copolymer; numerous other water-soluble hair fixatives listed in the CTFA Handbook at pages 73-74, incorporated herein by reference; and mixtures thereof. Numerous hair fixatives also are disclosed in U.S. Pat. No. 5,277,899, incorporated herein by reference. Particularly preferred are polyethylene oxide-polypropylene oxide random or block copolymers (eg, the Pluronic polymers which are polyethylene oxide(EO)-polypropylene oxide(PO)-polyethylene oxide(EO) block copolymers) and PVP (polyvinylpyrrolidone) polymers or copolymers thereof.

Other hair benefit agents include water-soluble hair dyes, such as, but not limited to, m-aminophenol hydrochloride, p-aminophenol sulfate, 2,3-diaminophenol hydrochloride, 1,5-naphthalenediol, p-phenylenediamine hydrochloride, sodium picramate, water-soluble cationic dyes, water-soluble anionic dyes, water-soluble FD&C dyes, like Blue No. 1, Blue No. 2, Red No. 3, Red No. 4, or Red No. 40, water-soluble D&C dyes, like Yellow No. 10, Red No. 22 or Red No. 28, and pyrogallol. Numerous other hair dyes are listed in the CTFA Handbook, pages 70-71, incorporated herein by reference.

The hydrophilic phase may comprise an antioxidant, like ascorbic acid or erythorbic acid; or a fluorescent whitening agent or optical brightener, like a distyrylbiphenyl derivative, stilbene or a stilbene derivative, a pyralozine derivative or a coumarin derivative. In addition, a hair growth promoter, or a hair bleaching agent, like a perborate or a persulfate salt, can be the hair benefit agent.

In addition, other compounds can be included in the hydrophilic phase in an amount sufficient to perform their intended function. For example, if the composition is intended to be a sunscreen, then compounds such as benzophenone-4, trihydroxycinnamic acid and salts, tannic acid, uric acid, quinine salts, dihydroxy naphtholic acid; an anthranilate, diethanolamine methoxynamate, p-aminobenzoic acid, phenylbenzimidazole sulfonic acid, PEG-25 p-aminobenzoic acid or triethanolamine salicylate can be incorporated.

Further, sunscreen compounds such as dioxybenzone, ethyl 4-[bis(hydroxypropyl)] aminobenzoate, glyceryl aminobenzoate, homosalate, menthyl anthranilate, octocrylene, octyl methoxycinnamate, octyl salicylate, oxybenzone, padimate O, red petrolatum, titanium dioxide, 4-menthylbenzylidene camphor, benzophenone-1, benzophenone-2, benzophenone-6, benzophenone-12, isopropyl dibenzoyl methane, butyl methoxydibenzoylmethane, zotocrylene, or zinc oxide can be incorporated. Other sunscreen compounds soluble in either the aqueous or organic phase are listed in CTFA Handbook, pages 86 and 87, incorporated herein by reference.

Similarly, topically-active drugs, like antifungal compounds; antibacterial compounds; anti-inflammatory compounds; topical anesthetics; skin rash, skin disease and dermatitis medications; and anti-itch and irritation-reducing compounds can be included in the compositions of the present invention. For example, analgesics such as benzocaine, dyclonine hydrochloride, aloe vera and the like; anesthetics such as butambenpicrate, lidocaine hydrochloride, xylocaine and the like; antibacterials and antiseptics, such as povidone-iodine, polymyxin b sulfate-bacitracin, zinc-neomycin sulfate-hydrocortisone, chloramphenicol, methylbenzethonium chloride, and erythromycin and the like; antiparasitics, such as lindane; antifungal agents such as zinc pyrithione, climbazole, ketoconazole and octapirox; anti-inflammatory agents, such as alclometasone dipropionate, betamethasone valerate, and the like; emollients and moisturizers, such as mineral oil, PEG-4 dilaurate, lanolin oil, petrolatum, mineral wax and the like; fungicides, such as butocouazole nitrate, haloprogin, clotrimazole, and the like. Any other medication capable of topical administration also can be incorporated in a composition of the present invention in an amount sufficient to perform its intended function. Other suitable compounds are listed in Remington's Pharmaceutical Sciences, 17th Ed., Merck Publishing Co., Easton, Pa. (1985), pages 773-791 and pages 1054-1058 (hereinafter Remington's), incorporated herein by reference.

The one or compounds of the hydrophilic phase are designed to remain on the skin or hair to perform the intended function. However, in particular situations, one or materials that is or are rinsed from the skin or hair can be incorporated into the hydrophilic phase.

The hydrophilic phase also can include optional ingredients traditionally included in topically-applied compositions. These optional ingredients include, but are not limited to, dyes, fragrances, preservatives, antioxidants, detackifying agents, and similar types of compounds. The optional ingredients are included in the hydrophilic phase in an amount sufficient to perform their intended function.

The hydrophilic phase is retained within the non-aqueous phase. By this we mean that the hydrophilic phase is associated with the non-aqueous phase such that it becomes more freely available after the non-aqueous phase melts. Thus, the hydrophilic phase may be present as one, two or more discrete regions inside and/or at the surface of the non-aqueous phase in each particle.

The particles of the invention preferably comprise a population in which at least 90% by weight of the particles (preferably at least 95% more preferably substantially all) of the particles have an average maximum dimension of from 10 nanometres (nm) to 300 microns ($\mu$m), preferably from 0.1 $\mu$m to 300 $\mu$m, more preferably 0.5 $\mu$m to 100 $\mu$m, even more preferably from 1 $\mu$m to 80 $\mu$m, such as from 1 $\mu$m to 20 $\mu$m. The maximum dimension of the particles will be the diameter when the particles are spherical and will otherwise be the greatest distance in a straight line across the particle. Average particle sizes can be determined by light microscopy.

The particles of the invention may be provided as, for example, a Gaussian or skewed, monomodal, multimodal or polymodal particle distribution.

Compositions of the Invention

Compositions of the invention may comprise the particles suspended, or otherwise dispersed, in a cosmetically acceptable diluent or carrier, as described hereinafter, such as an aqueous liquid (for example comprising at least 50% by weight water, preferably at least 75% by weight water).

Compositions of the invention can be leave on or rinse off compositions. Rinse off compositions are intended to be rinsed from the hair after use, although a minor proportion of the composition, including at least some of the particles, will remain on the hair after rinsing. Leave on products are applied to the hair and need not be rinsed off the hair after this application.

Compositions of the present invention are hair care compositions and can be formulated into a wide variety of product types, including mousses, gels, lotions, tonics, sprays, shampoos, conditioners, rinses, and the like. Compositions of the invention comprise, in addition to the particles, a cosmetically acceptable diluent or carrier.

Compositions of the present invention can comprise a carrier, or a mixture of such carriers, which are suitable for application to the hair. The carriers are present at from about 0.5% to about 99.5%, preferably from about 5.0% to about 99.5%, more preferably from about 10.0% to about 98.0%, by weight of the composition. As used herein, the phrase "suitable for application to hair" means that the carrier does not damage or negatively affect the aesthetics of hair or cause irritation to the underlying skin.

Carriers suitable for use with hair care compositions of the present invention include, for example, those used in the formulation of hair sprays, mousses, tonics, gels, shampoos, conditioners, and rinses. The choice of appropriate carrier will also depend on the particular formulation, and whether the product formulated is meant to be left on the surface to which it is applied (e.g., hair spray, mousse, tonic, or gel) or rinsed off after use (e.g., shampoo, conditioner or rinse).

The carriers used herein can include a wide range of components conventionally used in hair care compositions. The carriers can contain a solvent to disperse the particles being used, with water, the $C_1$-$C_6$ alcohols, lower alkyl acetate and mixtures thereof being preferred. The carriers can also contain a wide variety of additional materials such as acetone, hydrocarbons (such as isobutane, hexane, decene), halogenated hydrocarbons (such as Freons) and volatile silicones such as cyclomethicone.

Where the hair care compositions are conditioners and rinses, the carrier can include a wide variety of conditioning materials. Where the hair care compositions are shampoos, the carrier can include, for example, surfactants, suspending agents, and thickeners. Hair styling creams or gels also typically contain a structurant or thickener, typically in an amount of from 0.01% to 10% by weight.

The carrier can be in a wide variety of forms. For example, emulsion carriers, including oil-in-water, water-in-oil, water-in-oil-in-water, and oil-in-water-in-silicone emulsions, are useful herein. These emulsions can cover a broad range of viscosities, e.g., from about 100 cps to about 200,000 cps. Other suitable topical carriers include anhydrous liquid solvents such as oils, alcohols, and silicones (e.g., mineral oil, ethanol, isopropanol, dimethicone, cyclomethicone, and the like); aqueous-based single phase liquid solvents (e.g., hydro-alcoholic solvent systems); and thickened versions of these anhydrous and aqueous-based single phase solvents (e.g., where the viscosity of the solvent has been increased to form a solid or semi-solid by the addition of appropriate gums, resins, waxes, polymers, salts, and the like).

Compositions of the invention typically contain up to 50% by weight of the composition of the particles of the invention, preferably from 0.01% to 50% by weight, more preferably from 0.05% to 30% by weight, such as 1% to 20% by weight.

The following describes components that may be contained in compositions of the invention separate from the particles ie, in a separate phase from the particles and generally in the phase in which the particles are dispersed or suspended.

Shampoo and Hair Conditioning Compositions

Examples of rinse off compositions of the invention are shampoo compositions and hair conditioning compositions.

Shampoo compositions of the invention comprise, in addition to the particles, at least one surfactant which provides a deterging benefit. The deterging surfactant is preferably selected from anionic, nonionic, amphoteric and zwitterionic surfactants, and mixtures thereof.

Suitable anionic surfactants include the alkyl sulphates, alkyl ether sulphates, alkaryl sulphonates, alkanoyl isethionates, alkyl succinates, alkyl sulphosuccinates, N-alkoyl sarcosinates, alkyl phosphates, alkyl ether phosphates, alkyl ether carboxylates, and alpha-olefin sulphonates, especially their sodium, magnesium ammonium and mono-, di- and triethanolamine salts.

The most preferred anionic surfactants are sodium lauryl sulphate, triethanolamine lauryl sulphate, triethanolamine monolauryl phosphate, sodium lauryl ether sulphate 1EO, 2EO and 3EO, ammonium lauryl sulphate and ammonium lauryl ether sulphate 1EO, 2EO and 3EO.

Nonionic surfactants suitable for use in compositions of the invention may include condensation products of aliphatic ($C_8$-$C_{18}$) primary or secondary linear or branched chain alcohols or phenols with alkylene oxides, usually ethylene oxide and generally having from 6 to 30 ethylene oxide groups. Other suitable nonionics include mono- or di-alkyl alkanolamides. Example include coco mono- or di-ethanolamide and coco mono-isopropanolamide.

Further nonionic surfactants which can be included in shampoos for the invention are the alkyl polyglycosides (APGs). Typically, the APG is one which comprises an alkyl group connected (optionally via a bridging group) to a block of one or more glycosyl groups. Preferred APGs are defined by the following formula:

RO—(G)$_n$ wherein R is a branched or straight chain alkyl group which may be saturated or unsaturated and G is a saccharide group. Suitable alkyl polyglycosides for use in the invention are commercially available and include for example those materials identified as: Oramix NS10 ex Seppic; Plantaren 1200 and Plantaren 2000 ex Henkel.

Amphoteric and zwitterionic surfactants suitable for use in compositions of the invention may include alkyl amine oxides, alkyl betaines, alkyl amidopropyl betaines, alkyl sulphobetaines (sultaines), alkyl glycinates, alkyl carboxyglycinates, alkyl amphopropionates, alkylamphoglycinates alkyl amidopropyl hydroxysultaines, acyl taurates and acyl glutamates, wherein the alkyl and acyl groups have from 8 to 19 carbon atoms. Examples include lauryl amine oxide, cocodimethyl sulphopropyl betaine and preferably lauryl betaine, cocamidopropyl betaine and sodium cocamphopropionate.

The surfactants are present in shampoo compositions of the invention in an amount of from 1 to 50% by weight of the composition, preferably from 1 to 30% by weight, more preferably from 5 to 30% by weight.

Compositions in accordance with the invention may also take the form of hair conditioning compositions, which may be rinse off or leave-on hair conditioning compositions or so-called 2 in 1 compositions containing shampoo and conditioner. The conditioning compositions preferably comprise, in addition to the particles, one or more cationic surfactants. The use of cationic surfactants is especially preferred, because these ingredients are capable of providing conditioning benefits to hair.

Examples of cationic surfactants include the quaternary ammonium compounds mentioned hereinbefore as optional components of the hydrophilic phase. These include: quaternary ammonium hydroxides, e.g., tetramethylammonium hydroxide, alkyltrimethylammonium hydroxides wherein the alkyl group has from about 8 to 22 carbon atoms, for example octyltrimethylammonium hydroxide, dodecyltrimethy-ammonium hydroxide, hexadecyltrimethylammonium hydroxide, cetyltrimethylammonium hydroxide, octyldimethylbenzylammonium hydroxide, decyldimethyl-benzylammonium hydroxide, stearyldi-methylbenzylammonium hydroxide, didodecyldimethylammonium hydroxide, dioctadecyldimethylammonium hydroxide, tallow trimethylammonium hydroxide, cocotrimethylammonium hydroxide, and the corresponding salts thereof containing anions other than hydroxide, e.g., chlorides, Cetylpyridinium hydroxide or salts thereof (e.g., chloride), Quaternium-5, Quaternium-31, Quaternium-18, and mixtures thereof.

In hair conditioning compositions according to the invention, the level of cationic surfactant is preferably from 0.01 to 10%, more preferably 0.05 to 5%, most preferably 0.1 to 2% by weight of the composition.

Although the silicone wax used in the compositions of the invention can provide all or part of the conditioning benefits of the compositions, hair conditioning and shampoo compositions of the invention may both also contain one or more additional conditioning agents, preferably selected from silicones, protein hydrolysates and quaternised protein hydrolysates and other materials which are known in the art as having desirable hair conditioning properties.

Silicones are the most preferred conditioning agents and have been found to exhibit surprisingly superior properties when used in combination with the particles of the invention. The silicones are preferably in the form of liquid droplets, typically dispersed in compositions of the invention, preferably in an amount of from 0.01% to 5% by weight of the composition, more preferably from 0.1% to 5% by weight Suitable silicones include volatile and non-volatile silicones, such as for example polyalkylsiloxanes, polyalkylaryl siloxanes, siloxane gums and resins, cyclomethicones, aminofunctional silicones, quaternary silicones and mixtures thereof. Silicone oil is a particularly preferred conditioning agent for hair. The silicone may be in the form of a low viscosity oil which may contain a high viscosity oil or gum in solution. Alternatively, the high viscosity material may be in the form of an emulsion in water. The emulsion may be of high viscosity oil or of a solution of gum in a lower viscosity oil. The particle size of the oil phase may be anywhere in the range from 30 nanometres to up to 20 microns average size.

The silicone oil may suitably be a polydimethylsiloxane with an average particle size of less than 20 microns and preferably less than 2 microns. Small particle size enables a more uniform distribution of silicone conditioning agent for the same concentration of silicone in the composition. Advantageously, a silicone with a viscosity in the range 1-20 million cst is used. The silicone can be cross-linked.

Preferred silicones include polydimethylsiloxanes (of CTFA designation dimethicone) and hydroxylated polydimethylsiloxanes (of CTFA designation dimethiconol). Silicones of the above types are widely available commercially, for example as DC-1784 and DCX2-1391, both ex Dow Corning.

Suitable protein hydrolysates include lauryl dimonium hydroxy propylamino hydrolysed animal protein, available commercially under the trade name LAMEQUAT L, and hydrolysed keratin containing sulphur-bearing amino acids, available commercially under the trade name CROQUAT WKP.

In accordance with the invention, the hair shampoo and/or conditioner composition may also comprise a polymeric water-soluble cationic polymer as a conditioning agent.

The cationic polymer may be present at levels of from 0.01 to 5%, preferably from about 0.05 to 1%, more preferably from about 0.08% to about 0.5% by weight.

Synthetic or naturally derived polymers having a quaternised nitrogen atom are useful. The molecular weight of the polymer (in g/mol) will generally be between 5 000 and 10 000 000, typically at least 10 000 and preferably in the range 100 000 to about 2 000 000.

Representative synthetic quaternised polymers include, for example: cationic copolymers of 1-vinyl-2-pyrrolidine and 1-vinyl-3-methyl-imidazolium salt (e.g., Chloride salt) (referred to in the industry by the Cosmetic, Toiletry, and Fragrance Association, "CTFA". as Polyquaternium-16); copolymers of 1-vinyl-2-pyrrolidine and dimethylaminoethyl methacrylate (referred to in the industry by CTFA as Polyquaternium-11); cationic diallyl quaternary ammonium-containing polymers including, for example, dimethyldiallylammonium chloride homopolymer (referred to in the industry (CTFA) as Polyquaternium 6); mineral acid salts of amino-alkyl esters of homo-and co-polymers of unsaturated carboxylic acids having from 3 to 5 carbon atoms, as described in U.S. Pat. No. 4,009,256; and cationic polyacrylamides as described in WO95/22311.

Representative naturally-derived quaternised polymers include quaternised cellulosic compounds and cationic guar gum derivatives, such as guar hydroxypropyltrimonium chloride. Examples are JAGUAR C-13S, JAGUAR C-15, and JAGUAR-C17, commercially available from Meyhall in their JAGUAR (trademark) series.

Suitable cationic polyacrylamides are described in WO 95/22311 whose contents are incorporated herein by reference.

The compositions may further comprise from 0.1 to 5% of a suspending agent. Examples are polyacrylic acids, cross linked polymers of acrylic acid, copolymers of acrylic acid with a hydrophobic monomer, copolymers of carboxylic acid-containing monomers and acrylic esters, cross-linked copolymers of acrylic acid and acrylate esters, heteropolysaccharide gums and crystalline long chain acyl derivatives. The long chain acyl derivative is desirably selected from ethylene glycol stearates, alkanolamides of fatty acids having from 16 to 22 carbon atoms and mixtures thereof. Polyacrylic acid is available commercially as Carbopol 420, Carbopol 488 or Carbopol 493. Polymers of acrylic acid cross-linked with a polyfunctional agent may also be used, they are available commercially as Carbopol 910, Carbopol 934, Carbopol 940, Carbopol 941 and Carbopol 980. An example of a suitable copolymer of a carboxylic acid containing a monomer and acrylic acid esters is Carbopol 1342. All Carbopol materials are available from Goodrich and Carbopol is a trade mark. A further suitable suspending agent is dihydrogenated tallow phthalic acid amide (available from Stepan under the trademark Stepan TAB-2).

Suitable cross linked polymers of acrylic acid and acrylate esters are Pemulen TR1 or Pemulen TR2. A suitable heteropolysaccharide gum is xanthan gum, for example that available as Kelzan mu.

Another ingredient that may advantageously be incorporated into shampoo and/or conditioning compositions of the invention is a fatty alcohol material. The use of these materials is especially preferred in conditioning compositions of the invention, in particular conditioning compositions which comprise one or more cationic surfactant materials. The combined use of fatty alcohol materials and cationic surfactants in conditioning compositions is believed to be especially advantageous, because this leads to the formation of a lamellar phase, wherein the cationic surfactant is dispersed.

Preferred fatty alcohols comprise from 8 to 22 carbon atoms, more preferably 16 to 20. Examples of preferred fatty alcohols are cetyl alcohol and stearyl alcohol. The use of these materials is also advantageous in that they contribute to the overall conditioning properties of compositions of the invention.

The level of fatty alcohol materials is conveniently from 0.01 to 10%, preferably from 0.1 to 5% by weight of the composition. The weight ratio of cationic surfactant to fatty alcohol is preferably from 10:1 to 1:10, more preferably from 4:1 to 1:8, most preferably from 1:1 to 1:4.

A further ingredient that may be desirably included in the shampoo and/or conditioning compositions is a pearlescent material. Suitable pearlescent materials include ethylene glycol distearate, ethylene glycol monostearate, guanine and titanium dioxide coated micas, bismuth oxychloride, and stearic monoethanol amide. The level of pearlescent material present in the composition is generally 0.1% to 5%, preferably from 0.3% to 3% by weight of the composition.

The compositions of the invention may optionally comprise an antimicrobial agent. The antimicrobial agent may be a single compound or a mixture of two or more compounds. The antimicrobial agent may, for example, be in solid particulate form or dissolved in compositions of the invention.

The antimicrobial agent is typically present in compositions of the invention in an amount of from 0.01% to 5% by weight, preferably from 0.1% to 2% by weight.

Preferably, the antimicrobial agent is selected from climbazole, ketoconazole, octapirox and mixtures thereof. More preferably, the antimicrobial agent is climbazole. These antimicrobial agents will typically be in solution in compositions of the invention.

The preferred solid antimicrobial agents are metal pyrithiones, particularly zinc pyrithione (ZnPTO) which, on account of its relative insolubility in aqueous systems, is generally used in hair treatment compositions as a particulate dispersion. The zinc pyrithione may be used in any particle form including, for example, crystalline forms such as platelets and needles and amorphous, regularly or irregularly shaped particles. If zinc pyrithione is present in the composition, a suspending agent is preferably used to prevent or inhibit the settling of the particles out of the composition. The average particle diameter of the zinc pyrithione particles (ie, their maximum dimension) is typically from about 0.2 to about 50 μm, preferably from about 0.4 to about 10 μm. Particle size can be measured using a Malvern Mastersizer (Malvern Instruments, Malvern, UK).

Antimicrobial agents typically display a minimum inhibitory concentration of about 50 mg/ml or less against Malassezia.

The shampoo and/or conditioner compositions of the invention are preferably aqueous based. The compositions suitably comprise water in amount of from about 20 to about 99% by weight of the total composition.

The shampoo and conditioner compositions of the present invention may also contain other ingredients conventionally used in the art such as diluents, sequestrants, thickeners, carriers, antioxidants, proteins, polypeptides, preservatives, moisturising agents, solvents, perfumes, enzymes and polymers.

Leave on Products

When the hair care composition is a leave on product such as tonic or gel, the preferred solvents include water, ethanol, volatile silicone derivatives, and mixtures thereof. The solvents used in such mixtures may be miscible or immiscible with each other.

A tonic having a low viscosity may also utilise an emulsifying agent. Examples of suitable emulsifying agents include nonionic, cationic, anionic surfactants, or mixtures thereof. If such an emulsifying agent is used, it is preferably present at a level of from about 0.01% to about 7.5% by weight based on total weight of the composition. The level of propellant can be adjusted as desired but is generally from about 3% to about 30% by weight based on total weight for mousse compositions and from about 15% to about 50% by weight based on total weight for aerosol hair spray compositions.

A wide variety of additional components can be employed in leave on compositions, such as hair styling compositions, according to the present invention. Examples include the following:

hair styling polymers for hair styling compositions such as hair sprays, gels, and mousses. Hair styling polymers are well known articles of commerce and many such polymers are available commercially which contain moieties which render the polymers cationic, anionic, amphoteric or nonionic in nature. The polymers may be synthetic or naturally derived.

The amount of the polymer may range from 0.5 to 10%, preferably 0.75 to 6% by weight based on total weight of the composition.

Examples of anionic hair styling polymers are:

copolymers of vinyl acetate and crotonic acid;

terpolymers of vinyl acetate, crotonic acid and a vinyl ester of an alpha-branched saturated aliphatic monocarboxylic acid such as vinyl neodecanoate;

copolymers of methyl vinyl ether and maleic anhydride (molar ratio about 1:1) wherein such copolymers are 50% esterified with a saturated alcohol containing from 1 to 4 carbon atoms such as ethanol or butanol;

acrylic copolymers containing acrylic acid or methacrylic acid as the anionic radical-containing moiety with other monomers such as: esters of acrylic or methacrylic acid with one or more saturated alcohols having from 1 to 22 carbon atoms (such as methyl methacrylate, ethyl acrylate, ethyl methacrylate, n-butyl acrylate, t-butyl acrylate, t-butyl methacrylate, n-butyl methacrylate, n-hexyl acrylate, n-octyl acrylate, lauryl methacrylate and behenyl acrylate); glycols having from 1 to 6 carbon atoms (such as hydroxypropyl methacrylate and hydroxyethyl acrylate); styrene; vinyl caprolactam; vinyl acetate; acrylamide; alkyl acrylamides and methacrylamides having 1 to 8 carbon atoms in the alkyl group (such as methacrylamide, t-butyl acrylamide and n-octyl acrylamide); and other compatible unsaturated monomers.

The polymer may also contain grafted silicone, such as polydimethylsiloxane.

Specific examples of suitable anionic hair styling polymers are:

RESYN® 28-2930 available from National Starch (vinyl acetate/crotonic acid/vinyl neodecanoate copolymer);

ULTRAHOLD® 8 available from BASF (CTFA designation Acrylates/acrylamide copolymer);

the GANTREZ®ES series available from ISP corporation (esterified copolymers of methyl vinyl ether and maleic anhydride).

Other suitable anionic hair styling polymers include carboxylated polyurethanes. Carboxylated polyurethane resins are linear, hydroxyl-terminated copolymers having pendant carboxyl groups. They may be ethoxylated and/or propoxylated at least at one terminal end. The carboxyl group can be a carboxylic acid group or an ester group, wherein the alkyl moiety of the ester group contains one to three carbon atoms. The carboxylated polyurethane resin can also be a copolymer of polyvinylpyrrolidone and a polyurethane, having a CTFA designation PVP/polycarbamyl polyglycol ester. Suitable carboxylated polyurethane resins are disclosed in EP-A-0619111 and U.S. Pat. No. 5,000,955. Other suitable hydrophilic polyurethanes are disclosed in U.S. Pat. Nos. 3,822,238; 4,156,066; 4,156,067; 4,255,550; and 4,743,673.

Amphoteric hair styling polymers which can contain cationic groups derived from monomers such as t-butyl aminoethyl methacrylate as well as carboxyl groups derived from monomers such as acrylic acid or methacrylic acid can also be used in the present invention. One specific example of an amphoteric hair styling polymer is Amphomer® (Octylacrylamide/ acrylates/butylaminoethyl methacrylate copolymer) sold by the National Starch and Chemical Corporation.

Examples of nonionic hair styling polymers are homopolymers of N-vinylpyrrolidone and copolymers of N-vinylpyrrolidone with compatible nonionic monomers such as vinyl acetate. Nonionic polymers containing N-vinylpyrrolidone in various weight average molecular weights are available commercially from ISP Corporation—specific examples of such materials are homopolymers of N-vinylpyrrolidone having an average molecular weight of about 630,000 sold under the name PVP K-90 and are homopolymers of N-vinylpyrrolidone having an average molecular weight of about 1,200,000 sold under the name of PVP K-120.

Other suitable nonionic hair styling polymers are cross-linked silicone resins or gums. Specific examples include rigid silicone polymers such as those described in EP-A-0240350 and cross-linked silicone gums such as those described in WO 96/31188.

Examples of cationic hair styling polymers are copolymers of amino-functional acrylate monomers such as lower alkyl aminoalkyl acrylate, or methacrylate monomers such as dimethylaminoethyl methacrylate, with compatible monomers such as N-vinylpyrrolidone, vinyl caprolactam, alkyl methacrylates (such as methyl methacrylate and ethyl methacrylate) and alkyl acrylates (such as ethyl acrylate and n-butyl acrylate).

Specific examples of suitable cationic polymers are:
copolymers of N-vinylpyrrolidone and dimethylaminoethyl methacrylate, available from ISP Corporation as Copolymer 845, Copolymer 937 and Copolymer 958;
copolymers of N-vinylpyrrolidone and dimethylaminopropylacrylamide or methacrylamide, available from ISP Corporation as Styleze® CC10;
copolymers of N-vinylpyrrolidine and dimethylaminoethyl methacrylate;
copolymers of vinylcaprolactam, N-vinylpyrrolidone and dimethylaminoethylmethacrylate;
Polyquaternium-4 (a copolymer of diallyldimonium chloride and hydroxyethylcellulose);
Polyquaternium-11 (formed by the reaction of diethyl sulphate and a copolymer of vinyl pyrrolidone and dimethyl aminoethylmethacrylate), available from ISP as Gafquat® 734, 755 and 755N, and from BASF as Luviquat® PQ11;
Polyquaternium-16 (formed from methylvinylimidazolium chloride and vinylpyrrolidone), available from BASF as Luviquat® FC 370, FC 550, FC 905 and HM-552;
Polyquaternium-46 (prepared by the reaction of vinylcaprolactam and vinylpyrrolidone with methylvinylimidazolium methosulphate), available from BASF as Luviquat® Hold.

Examples of suitable naturally-derived polymers include shellac, alginates, gelatins, pectins, cellulose derivatives and chitosan or salts and derivatives thereof. Commercially available examples include Kytamer® (ex Amerchol) and Amaze® (ex National Starch).

Also suitable for use as optional components in the compositions of the invention are the ionic copolymers described in WO 93/03703, the polysiloxane-grafted polymers disclosed in WO 93/23446, the silicone-containing polycarboxylic acid copolymers described in WO 95/00106 or WO 95/32703, the thermoplastic elastomeric copolymers described in WO 95/01383, WO 95/06078, WO 95/06079 and WO 95/01384, the silicone grafted adhesive polymers disclosed in WO 95/04518 or WO 95/05800, the silicone macrografted copolymers taught in WO 96/21417, the silicone macromers of WO 96/32918, the adhesive polymers of WO 98/48770 or WO 98/48771 or WO 98/48772 or WO 98/48776, the graft polymers of WO 98/51261 and the grafted copolymers described in WO 98/51755.

With certain of the above-described polymers it may be necessary to neutralise some acidic groups to promote solubility/dispersibility. Examples of suitable neutralising agents include 2-amino-2-methyl-1,3-propanediol (AMPD); 2-amino-2-ethyl-1,3-propanediol (AEPD); 2-amino-2-methyl-1-propanol (AMP); 2-amino-1-butanol (AB); monoethanolamine (MEA); diethanolamine (DEA); triethanolamine (TEA); monoisopropanolamine (MIPA); diisopropanolamine (DIPA); triisopropanolamine (TIPA); and dimethyl stearamine (DMS). A long chain amine neutralising agent such as stearamidopropyl dimethylamine or lauramidopropyl dimethylamine may be employed, as is described in U.S. Pat. No. 4,874,604. Also suitable are inorganic neutralisers, examples of which include sodium hydroxide, potassium hydroxide and borax. Mixtures of any of the above neutralising agents may be used. Amounts of the neutralising agents will range from about 0.001 to about 10% by weight of the total composition.

sunscreening agents such as 2-ethylhexyl p-methoxycinnamate, 2-ethylhexyl N,N-dimethyl-p-aminobenzoate, p-aminobenzoic acid, 2-phenylbenzimidazole-5-sulfonic acid, octocrylene, oxybenzone, homomenthyl salicylate, octyl salicylate, 4,4'-methoxy-t-butyldibenzoylmethane, 4-isopropyl dibenzoylmethane, 3-benzylidene camphor, 3-(4-methylbenzylidene) camphor, titanium dioxide, zinc oxide, silica, iron oxide, and mixtures thereof.

anti-dandruff actives such as zinc pyrithione, piroctone olamine, selenium disulphide, sulphur, coal tar, and the like.

hair conditioning agents such as hydrocarbons, silicone fluids, and cationic materials. The hydrocarbons can be either straight or branched chain and can contain from about 10 to about 16, preferably from about 12 to about 16 carbon atoms. Examples of suitable hydrocarbons are decane, dodecane, tetradecane, tridecane, and mixtures thereof. Examples of suitable silicone conditioning agents useful herein can include either cyclic or linear polydimethylsiloxanes, phenyl and alkyl phenyl silicones, and silicone copolyols. Cationic conditioning agents useful herein can include quaternary ammonium salts, as mentioned hereinbefore as materials for incorporation into the aqueous phase, or the salts of fatty amines.

emulsifiers for emulsifying the various carrier components of the compositions of the invention. Suitable emulsifier types include polyethylene glycol 20 sorbitan monolaurate (Polysorbate 20), polyethylene glycol 5 soya sterol, Steareth-20, Ceteareth-20, PPG-2 methyl glucose ether distearate, Ceteth-10, Polysorbate 80, cetyl phosphate, potassium cetyl phosphate, diethanolamine cetyl phosphate, Polysorbate 60, glyceryl stearate, PEG-100 stearate, and mixtures thereof. The emulsifiers can be used individually or as a mixture of two or more and can comprise from about 0.1% to about 10%, more preferably from about 1% to about 7%, and most preferably from about 1% to about 5%, by weight based on total weight of the composition.

vitamins and derivatives thereof (e.g., ascorbic acid, vitamin E, tocopheryl acetate, retinoic acid, retinol, retinoids, and the like).

cationic polymers (e.g., cationic guar gum derivatives such as guar hydroxypropyltrimonium chloride and hydroxypropyl guar hydroxypropyltrimonium chloride, available as the Jaguar® series from Rhone-Poulenc).

preservatives, antioxidants, chelators and sequestrants; and aesthetic components such as fragrances, colourings, hair nutrients and essential oils.

Compositions of the invention are preferably used in the method of the invention.

The method of manufacturing these compositions is disclosed above. It is preferred if the temperature of the composition is on or below the solidification commencement temperature of the non-aqueous phase (wax), more preferably the temperature of the composition is 1.5° C. below the solidification commencement temperature of the non-aqueous phase (wax).

Further components may be added to the composition on cooling after/during the addition of particles of non aqueous phase/hydrophilic phase.

In the method of treatment of the invention, hair is treated with particles that can be used in compositions of the invention. The treatment preferably involves the use of a composition of the invention but other compositions comprising the particles may be used instead. Typically, the particles are applied to hair during a shampooing step or a hair conditioning step or a hair styling step or during two or all of these steps. In the case of rinse off products, after rinsing the compositions from the hair, at least some of the particles remain deposited on the hair.

At this stage of the method of the invention, the user of the product may experience some hair conditioning benefits if the hair is allowed to dry.

However, the method of the invention comprises a step of heating the hair treated with the particles to a temperature that is above the melting point of the particles. Following this heating step, the user of the product may experience improved hair conditioning benefits due to the silicone wax and any other hair conditioning material that is present in the particles. Without wishing to be bound by theory, it is believed that when the hair is heated to a temperature above the melting point of the particles, the constituents of the particles are able to flow and to spread onto the hair to provide a more even distribution of the constituents on the hair fibre. Also, the user of the composition may experience a greater benefit from any other material that is contained in the particles, following its release from the wax particles.

In the method of the invention, the hair may be heated whilst it is still wet eg, during drying at an elevated temperature eg, with a blow dryer or in a salon dryer.

Alternatively, the hair may be heated after it has been allowed to dry at room temperature. Other methods of heating include heating which takes place during styling of the hair eg, using curling tongs. The hair may be styled whilst it is wet or after it has been dried.

The temperature to which the hair is heated will depend on the melting point of the particles that are used. Typically, the hair is heated to a temperature of from 30° C. to 100° C., such as 35° C. to 90° C. eg, 40° C. to 70° C.

The invention will now be described with reference to the following non-limiting examples. In the examples and throughout this specification, all percentages are by weight based on total composition and based on active material unless indicated otherwise.

EXAMPLES

Particle sizes were measured using an Olympus BH-2 Transmission microscope. The particle size is measured by:
1) placing a graticule on the microscope platform
2) changing the magnification to 20 times focus and adjusting the focus until the graticule can be clearly seen
3) printing out a picture of the graticule
4) using a ruler to calculate the distance in millimetres on the picture covered by 100 microns on the graticule
5) placing a sample on the microscope slide and keeping magnification at 20 times focus
6) adjusting focus so the particles in the sample can clearly be seen
7) printing out a picture of the particles in the sample
8) calculating the average size of the particles in microns by measuring the diameters (or the longest dimension) of the particles in millimetres and converting into microns by using the calculation from step 4.

Melting points of the particles were determined by Differential Scanning Calorimetry (DSC). DSC measurements were performed on a Perkin-Elmer DSC 7 series at a heating rate of 10° C. per minute. Heating rates of 5° C. per minute could be used for materials having a slow crystallisation rate (although this did not apply to the waxes used in these examples).

The re-solidification temperature is measured as follows:
i) heating the non-aqueous material to 10° C. above its melting point;
ii) once the non-aqueous material is completely molten cooling at 3-5° C. intervals
iii) at each of these intervals the viscosity is measured and the temperature recorded
iv) the re-solidification temperature is the temperature at which the viscosity of the non-aqueous material increases.

In the following formulations, figures are percentages by weight of active material based on total formulation.

Example 1

Delivery of style benefits from a conditioner containing silicone wax encapsulating styling polymer:

The following conditioner (control) formulation and composition of the invention (silicone wax encapsulating an aqueous solution of PVP K90) were prepared:

| Trade name | Chemical Name | Conditioner % w/w active | Example 1 % w/w active |
| --- | --- | --- | --- |
| Arquad 16-29 | Cetrimonium Chloride | 2.80 | 2.80 |
| Arquad 2HT | Ditallow Dimethyl ammonium chloride | 0.50 | 0.50 |
| Laurex CS | Cetyl/stearyl alcohol | 3.00 | 3.00 |
| Natrosol HHR | Hydroxy ethyl cellulose | 0.20 | 0.20 |
| EDTA | Tetrasodium EDTA | 0.10 | 0.10 |
| Potassium Chloride | Potassium Chloride | 0.30 | 0.30 |
| DC1786 | Poly dimethyl siloxane | 1.6 | — |
| Arosurf TA100 | Distearyl dimethyl ammonium chloride | — | 0.10 |
| Luviskol PVP K90 | Polyvinyl pyrrolidone | — | 1.2 |
| Abil EM 90 | Modified polyether polysiloxane | — | 0.187 |
| Abil EM 97 | Alpha, omega polyethersiloxane | — | 0.063 |
| Sodium Chloride | Sodium Chloride | — | 0.40 |
| Silicone Wax (Dow Corning) | | — | 2.325 |
| Isopropyl palmitate | Isopropyl palmitate | 2.325 | 2.325 |
| Preservative | | q.s. | q.s. |
| Water | | To 100% | To 100% |

The composition of Example 1 was prepared as follows:
1) Heat the wax together with Abil EM90, Abil EM97 and Arosurf TA100 to 70° C. in water bath.
2) In a separate beaker heat the PVP K90 solution to 70° C.
3) Add the PVP solution slowly to the hot wax mixture under shear.
4) Once all the PVP has been incorporated, continue to shear the mixture for 10 minutes maintaining the temperature at 70° C.
5) The resultant emulsion is then added to the conditioner base at about 50° C. under low shear.

The particles were found to have an average size of 18 microns.

Results:

Mannequin Head Evaluation:

Mannequin heads were wet thoroughly and to each side of the head 4 g of a shampoo was applied. The shampoo was massaged into the head for 30 seconds then rinsed for 30 seconds on each side. The application and massage was then repeated with a final rinse lasting 1 minute on each side. 4 g of control conditioner was then added to the left side of the head, massaged for 1 minute and then rinsed for 1 minute. 4 g of the conditioner of Example 1 was added to the right side of the head, massaged for 1 minute and then rinsed for 1 minute. The entire head was then heat styled (using a brush and blow dryer) by an expert hair stylist. The dried, styled heads were then assessed for a range of attributes by 12 panellists. The results shown were obtained by scoring—1 if the panellist preferred the left hand side (Control), 0 if they saw no difference and 1 if they preferred the right hand side (Example 1). The amounts from 12 panellists were then added together to give the final value which has been used to derive the data in the table below. The amount that they deviate from 0 shows the preference for one side over the other with a positive value showing that the right hand side (Example 1 side) was preferred and a negative value indicating that the left hand side (control side) was preferred.

| | Control | Example 1 |
| --- | --- | --- |
| Root Lift | 0 | 10 |
| Volume | 0 | 10 |
| Body | 0 | 6 |

Example 2

Delivery of style benefits from a conditioner containing wax encapsulating styling polymer.

The following control conditioner formulation and composition of the invention (vegetable wax encapsulating an aqueous solution of PVP K90; Example 2) were prepared

| Trade name | Chemical Name | Control (% w/w) | Example 2 (% w/w) |
| --- | --- | --- | --- |
| Arquad 16-29 | Cetrimonium Chloride | 2.80 | 2.80 |
| Arquad 2HT | Ditallow Dimethyl ammonium chloride | 0.50 | 0.50 |
| Laurex CS | Cetyl/stearyl alcohol | 3.00 | 3.00 |
| Natrosol HHR | Hydroxy ethyl cellulose | 0.20 | 0.20 |
| EDTA | Tetrasodium EDTA | 0.10 | 0.10 |
| Potassium Chloride | Potassium Chloride | 0.30 | 0.30 |
| DC 1786 | Poly dimethyl siloxane | 1.2 | |
| Luviskol PVP K90 | Polyvinyl pyrrolidone | — | 1.2 |
| Admul WOL | Polyglycerol polyricinoleate | — | 0.25 |
| Sodium Chloride | Sodium Chloride | 0.40 | 0.40 |
| Vegetable Vaseline E | Mixture of triacyl glycerols | — | 4.75 |
| Preservative | | q.s. | q.s. |
| Water | | To 100% | To 100% |

The composition of Example 2 was prepared as follows:
1) Heat the wax (vegetable vaseline E) together with Admul Wol to 70° C. in water bath.
2) In a separate beaker heat the PVP K90 solution to 70° C.
3) Add the PVP solution slowly to the hot wax mixture under shear.
4) Once all the PVP has been incorporated, continue to shear the mixture for 10 minutes maintaining the temperature at 70° C.
5) The resultant emulsion is then added to the conditioner base at about 50° C. under low shear.

The particles were found to have an average size of 22 microns.

Results:

The compositions were tested using a mannequin head evaluation test as described in Example 1.

| | Control | Example 2 |
| --- | --- | --- |
| Root Lift | 0 | 1 |
| Volume | 0 | 8 |
| Body | 0 | 8 |
| Ease of Comb | 0 | 6 |

Examples 3 and 4

Encapsulation of hydrophilic materials (Pluronic F127)
Example 3: Conditioner containing wax encapsulants with no Pluronic F127
Example 4: Conditioner containing wax encapsulating Pluronic F127
The following formulations were prepared:

| Trade Name | Chemical Name | Example 3 % w/w | Example 4 % w/w |
| --- | --- | --- | --- |
| Arquad 16-29 | Cetrimonium Chloride | 2.80 | 2.80 |
| Arquad 2HT | Ditallow Dimethyl ammonium chloride | 0.50 | 0.50 |
| Laurex CS | Cetyl/stearyl alcohol | 3.00 | 3.00 |
| Natrosol HHR | Hydroxy ethyl cellulose | 0.20 | 0.20 |
| Propylene Glycol | Propylene Glycol | | 10.72 |
| EDTA | Tetrasodium EDTA | 0.10 | 0.10 |
| Potassium Chloride | Potassium Chloride | 0.30 | 0.30 |
| Abil 2440 | Behenoxy dimethicone | 1.63 | 1.63 |
| Abil 9810 | C24-28 alkyl methicone | 3.36 | 3.36 |
| Pluronic F127 | EO-PEO-EO Block Copolymer | | 3.33 |
| Arosurf TA100 | Distearyl dimethyl ammonium chloride | 0.10 | 0.10 |
| Genapol C050 | Coco 5EO alcohol ethoxylate | | 0.44 |
| Preservative | | q.s. | q.s. |
| Water | | To 100% | To 100% |

The composition of Example 4 was prepared as follows:
a. Abil 2440 and Abil 9810 and Arosurf TA100 were mixed with coco 5EO in a beaker placed in a water bath at 70° C. until melted.
b. Pluronic F127 was placed in a water bath at 70° C. until melted.
c. Propylene glycol was placed in a beaker and heated to 70° C. in a water bath.
d. The molten Pluronic F127 was sheared into the molten wax for 5 minutes.
e. The molten wax/Pluronic F127 mixture was poured into the hot propylene glycol under shear for 2 minutes.
f. Distilled water was cooled to 10° C. in a large beaker.
g. The wax-in-propylene glycol emulsion was quickly poured into the cold water, under continuous rapid stirring.
h. Dispersion was added to a conditioner base with a 10% gap such that the wax totaled 5% by weight in the final formulation.

The particles were found to have an average size of 22 microns.

The composition of Example 3 was prepared as follows:
a. Abil 2440 and Abil 9810 and Arosurf TA100 were mixed with coco 5EO in a beaker placed in a water bath at 70° C. until melted.
b. Propylene glycol was placed in a beaker in the same water bath.
c. The molten wax was poured into the hot propylene glycol under shear for 2 minutes.
d. Distilled water was cooled to 10° C. in a large beaker.
e. The wax-in-propylene glycol emulsion was quickly poured into the cold water, under continuous rapid stirring.
f. Dispersion was added to a conditioner base with a 10% gap such that the wax totaled 5% in the final formulation.

Results:
The compositions were tested in a mannequin head evaluation as described in Example 1.

| | Example 3 | Example 4 |
| --- | --- | --- |
| Root Lift | 0 | 6 |
| Volume | 0 | 9 |
| Body | 0 | 9 |
| Ease of Comb | 0 | 3 |

Example 5

Conditioning benefits from a shampoo containing wax encapsulating a concentrated conditioner (shampoo containing 5% by weight enapsulated conditioner particles (70/30 by weight wax/conditioner)).

| Trade Name | Chemical Name | Shampoo % w/w | Example 5 % w/w |
| --- | --- | --- | --- |
| Surfactant blend* | | 24.00 | 24.00 |
| Jaguar C13 S | Guar hydroxypropyl trimonium chloride | 0.10 | 0.10 |
| Carbopol 980 | Carbomer | 0.40 | 0.40 |
| Arquad 16-29 | Cetrimonium Chloride | — | 0.19 |
| Arquad 2HT | Ditallow Dimethyl ammonium chloride | — | 0.04 |
| Laurex CS | Cetyl/stearyl alcohol | — | 0.21 |
| Propylene Glycol | Propylene Glycol | 0.50 | 0.50 |
| Ammonium Chloride | Ammonium Chloride | — | 1.2 |
| Sodium Hydroxide | Sodium Hydroxide | To adjust pH | To adjust pH |
| Abil 2440 | Behenoxy dimethicone | — | 3.26 |
| Arosurf TA100 | Distearyl dimethyl ammonium chloride | — | 0.07 |
| Abil EM 90 | Modified polyether polysiloxane | — | 0.13 |
| Abil EM 97 | Alpha, omega polyethersiloxane | — | 0.04 |
| Preservative | | q.s. | q.s. |
| Water | | To 100% | To 100% |

*ammonium lauryl sulphate - 29.25 wt %, ammonium laureth sulphate 2 mole - 22.85 wt %, cocamide MEA - 5.00 wt %, PEG-5 cocamide - 2.50 wt %

Methodology:
Preparation of Concentrated Conditioner:
1) Heat water to 75° C. using a water bath.
2) Add the cetrimonium chloride and the ditallow dimethyl ammonium chloride to the water and allow to melt and disperse.
3) Once the resulting mixture is at 75° C. add the cetyl/stearyl alcohol and mix for 30 minutes at 75° C.
4) Remove from heat and cool to 30° C. whilst stirring.

Preparation of Concentrated Conditioner Wax Encapsulates in Shampoo
1) In a beaker in a water bath heat the shampoo base to ~50° C.
2) In a separate beaker melt the concentrated conditioner together with the wax (Abil 2440), Arosurf TA100, Abil EM 90 and Abil EM97 at 50° C.
3) Add the molten wax/concentrated conditioner mixture to the hot shampoo whilst stirring. Allow to mix for about 1 minute.
4) Remove from heat and cool with stirring to ambient.

The particles were found to have an average size of 4 microns.

Results:

The compositions were tested in a mannequin head evaluation as described in Example 1.

|  | Shampoo | Example 5 |
|---|---|---|
| Ease of Comb | 0 | 7 |

Example 6

Silicone wax microparticles encapsulating a hair dye were formulated as follows:

| Trade Name | Chemical Name | Example 6 % w/w |
|---|---|---|
| Cutina GMS | Glyceryl Monostearate | 10.00 |
| Abil 2440 | Behenoxy dimethicone | 89.00 |
| Arianor Mahogany Dye | Dye Basic Brown-16 | 1.00 |

The composition was prepared according to the following procedure:
1) The wax, Cutina GMS, and Arianor Mahogany Dye were heated to ~60° C.
2) 90 g of water was heated to 55° C.
3) Under shear, the hot water was quickly added to the wax/dye melt.
4) The water/wax/dye mixture was then quickly added to ~300 g of ice cold water (~4° C.) under shear.
5) Once the particles had solidified, they were filtered to remove excess water.
6) The particles were then washed with water and re-filtered several times to remove excess dye. The particles were washed until the filtrate was clear.

Results:

The change in colour (Delta E) was determined when hair treated with the composition was air dried and when it was heat dried.
1) 50 mm (2")/0.75 g Yak Hair switches were measured on the HunterLab ColourQuest Spectrophotometer to give a baseline reading before commencing the experiments.
2) The switch was pre-wet with 2 g water.
3) 1 g of wax microparticles encapsulating a hair dye solution was applied as evenly as possible to the switch.
4) The switch was then left for 5 minutes at the measurement temperature—room temperature or 55° C.
5) The particles were then rubbed into the switch for 1 minute.
6) Excess wax was then removed from the switch by washing with 0.08 g of shampoo/0.72 g water for 30 s and then rinsed under running water for 30 s.
7) This was repeated a further two times (3 washes in total).
8) The switch was then allowed to dry naturally at room temperature and was then measured on the Spectrophotometer.
9) Differences in the measurements before and after treatment are expressed as Delta E values.

|  | Wax encapsulating hair dye - Air Dried | Wax encapsulating hair dye - Hot Dried |
|---|---|---|
| Delta E | 1 | 9 |

Greater colour occurred after heating of the particles to release the encapsulated hair dye.

Example 7

The following is a further illustrative example of a conditioner composition according to the invention, which can be prepared using the method outlined in Example 4.

| Trade name | Chemical Name | Example 7 % w/w active |
|---|---|---|
| Ethoquad 0/12 PG | PEG-2 Oleamonium Chloride in PG | 2.00 |
| Laurex CS | Cetyl/stearyl alcohol | 7.00 |
| Propylene glycol | Propylene glycol | 10.72 |
| Abil 2440 | Behenoxy dimethicone | 1.63 |
| Arosurf TA100 | Distearyl dimethyl ammonium chloride | 0.10 |
| Abil 9810 | C24-28 alkyl methicone | 3.36 |
| Pluronic F108 | EO-PO-EO block copolymer | 3.33 |
| Genapol C050 | Coco 5EO alcohol ethoxylate | 0.44 |
| TS 100% Water, fragrance, preservative, etc. |  | To 100% |

The following conditioner composition of the invention (wax encapsulating an aqueous solution of PVP K90) was prepared:

Example 8

| Trade name | Chemical Name | Example 8 % w/w active |
|---|---|---|
| Arquad 16-29 | Cetrimonium Chloride | 2.80 |
| Arquad 2HT | Ditallow Dimethyl ammonium chloride | 0.50 |
| Laurex CS | Cetyl/stearyl alcohol | 3.00 |
| Natrosol HHR | Hydroxy ethyl cellulose | 0.20 |
| EDTA | Tetrasodium EDTA | 0.10 |
| Potassium Chloride | Potassum Chloride | 0.30 |
| DC1786 | Poly dimethyl siloxane | — |
| Luviskol PVP K90 | Polyvinyl pyrrolidone | 1.25 |
| Abil EM 90 | Modified polyether polysiloxane | 0.187 |
| Abil EM 97 | Alpha, omega polyethersiloxane | 0.063 |
| Citric acid anhydrous | Citric acid anhydrous | 0.01 |
| Abil 2440 wax |  | 4.75 |
| Preservative |  | q.s. |
| Water |  | To 100% |

The composition of Example 8 was prepared as follows:
1) Heat the wax together with Abil EM90 and Abil EM97 to 70° C. in water bath.
2) In a separate beaker heat the PVP K90 solution (20 wt %) to 70° C.
3) Add the PVP solution slowly to the hot wax mixture under shear.

4) Once all the PVP has been incorporated, continue to shear the mixture for 10 minutes maintaining the temperature at 70° C.
5) The resultant emulsion is then added to the conditioner base at about 49.5° C. under low shear.

PVP Capture: 24%.
Particle size range: 50-100 microns
Mp of wax: 42 deg C. (range 32 to 46 deg C.)
Solidification pt:46 deg C.
Abil 2440 Wax chemical name: Behenoxy dimethicone

The invention claimed is:

1. A method of treating hair which comprises:
   i) applying to the hair a hair treatment composition comprising 1 to 20% by weight of the composition of particles having a first hydrophobic, non-aqueous phase and, retained within said first non-aqueous phase, a second hydrophilic phase which is an aqueous solution, dispersion or emulsion or which is a solid or liquid having a log P value less than 1, said second phase comprising a hair benefit agent comprising one or more materials selected from the group consisting of hair fixatives, hair dyes, hair conditioners and mixtures thereof, wherein said first hydrophobic, non-aqueous phase has a melting point of from 30° C. to 100° C., wherein said first hydrophobic, non-aqueous phase is a silicone wax, and wherein at least 90% by weight of the particles have an average maximum dimension in the range of from 0.1 µm to 300 µm; and
   ii) heating the hair to a temperature above the melting point of the first hydrophobic, non-aqueous phases,
   wherein the silicone wax comprises one or more $C_3$ to $C_{40}$ branched or unbranched. saturated alkyl groups.

2. A method as claimed in claim 1, wherein at least 90% by weight of the particles an average maximum dimension of from 0.5 µm to 100 µm.

3. A method as claimed in claim 1 wherein the first hydrophobic, non-aqueous phase has a melting point of from 35° C. to 90° C.

4. A method as claimed in claim 3, wherein the first hydrophobic, non-aqueous phase has a melting point of from 40° C. to 70° C.

5. A method as claimed in claim 1, wherein the composition comprises the particles in an amount of from 0.01% to 50% by weight.

6. A method as claimed in claim 1, wherein the hair fixative is selected from polyethylene oxide-polypropylene oxide-polyethylene oxide block copolymers and polyvinylpyrrolidone polymers and polyvinylpyrrolidone copolymers thereof.

7. A method as claimed in claim 1, wherein the hydrophilic phase comprises water in an amount of from 10% to 99% by weight.

8. A method as claimed in claim 1 wherein the hair treatment composition is a leave on product.

9. A method as claimed in claim 8 wherein the hair treatment composition is a hair styling product selected from creams and gels.

10. A method as claimed in claim 1 wherein the hair treatment composition is a rinse off product.

11. A method as claimed in claim 10 wherein the hair treatment composition is a shampoo or conditioner.

12. A hair treatment composition comprising particles having a first hydrophobic, non-aqueous phase and, retained within said first hydrophobic, non-aqueous phase, a second hydrophilic phase which is an aqueous solution, dispersion or emulsion or which is a solid or liquid having a log P value less than 1, said second phase comprising a hair benefit agent, wherein said first hydrophobic, non-aqueous phase has melting point of from 30° C. to 100° C. wherein said first hydrophobic, non-aqueous phase is a silicone wax, and wherein at least 90% by weight of the particles have an average maximum dimension in the range of from 0.1 µm to 300 µm, wherein the silicone wax comprises one or more $C_3$ to $C_{40}$ branched or unbranched, saturated alkyl groups, and the hair benefit agent comprises one or more materials selected from the group consisting of hair fixatives, hair dyes, hair conditioners and mixtures thereof.

13. A method as described in claim 1 wherein the hair is rinsed following application of the hair treatment composition and is thereafter heated to temperature above the melting point of the first hydrophobic, non-aqueous phase during drying at elevated temperature or after being allowed to dry at room temperature said hair treatment composition being in the form of a rinse-off product.

* * * * *